(12) United States Patent
Soni et al.

(10) Patent No.: US 7,741,507 B2
(45) Date of Patent: Jun. 22, 2010

(54) PROCESS FOR PREPARING VALSARTAN

(75) Inventors: Rohit Ravikant Soni, Vadodara (IN); Sanjay Lakhabhai Vasoya, Vadodara (IN); Ravindra Charudatta Ghotikar, Vadodara (IN); Anand Kumar Pandey, Vadodara (IN); Hetal Remeshchandra Shah, Vadodara (IN)

(73) Assignee: Alembic Limited, Gujarat (IN)

( * ) Notice: Subject to any disclaimer, the term of this patent is extended or adjusted under 35 U.S.C. 154(b) by 850 days.

(21) Appl. No.: 11/491,638

(22) Filed: Jul. 24, 2006

(65) Prior Publication Data

US 2006/0258878 A1    Nov. 16, 2006

(30) Foreign Application Priority Data

Aug. 22, 2005   (IN)   .................. 992/MUM/2005

(51) Int. Cl.
   *C07C 255/00*   (2006.01)
(52) U.S. Cl. .................................................... 558/425
(58) Field of Classification Search ............... 558/425
   See application file for complete search history.

(56) References Cited

U.S. PATENT DOCUMENTS

| 5,399,578 | A * | 3/1995 | Buhlmayer et al. | 514/381 |
| 6,589,547 | B1 * | 7/2003 | Igari et al. | 424/426 |
| 2003/0068374 | A1 * | 4/2003 | Kamei et al. | 424/468 |

\* cited by examiner

*Primary Examiner*—Susannah Chung
(74) *Attorney, Agent, or Firm*—Hamre, Schumann, Mueller & Larson, P.C.

(57) ABSTRACT

The invention relates to novel compound of formula (IV), which is an organic acid salt of N-[(2'-cyanobiphenyl-4-yl) methyl]-(L)-valine ester. This compound is an useful intermediate for process of preparation of Valsartan of formula (I), chemically known as (S)—N-(1-Carboxy-2-methylprop-1-yl)-N-pentanoyl-N-[2'-(1H-tetrazol-5-yl)biphenyl-4-ylmethyl]amine. This invention also relates to a process for preparing Valsartan using novel intermediate of formula (IV).

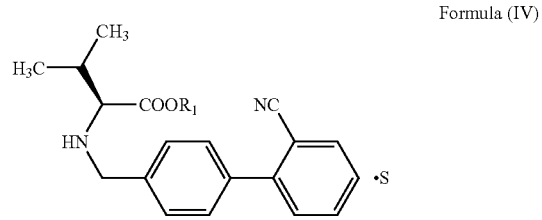

Formula (IV)

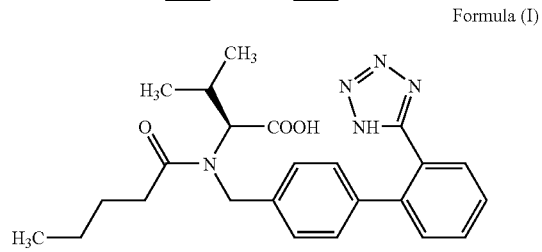

Formula (I)

4 Claims, No Drawings

PROCESS FOR PREPARING VALSARTAN

FIELD OF INVENTION

The present invention relates to novel compound of N-[(2'-cyanobiphenyl-4-yl)methyl]-(L)-valine ester organic acid salt of formula (IV), which is useful as an intermediate for the preparation of Valsartan of formula (I), chemically known as (S)—N-(1-Carboxy-2-methylprop-1-yl)-N-pentanoyl-N-[2'-(1H-tetrazol-5-yl)biphenyl-4-ylmethyl]amine. Valsartan is useful as an antihypertensive. The present invention also relates to a process for preparing Valsartan using novel intermediate of formula (IV),

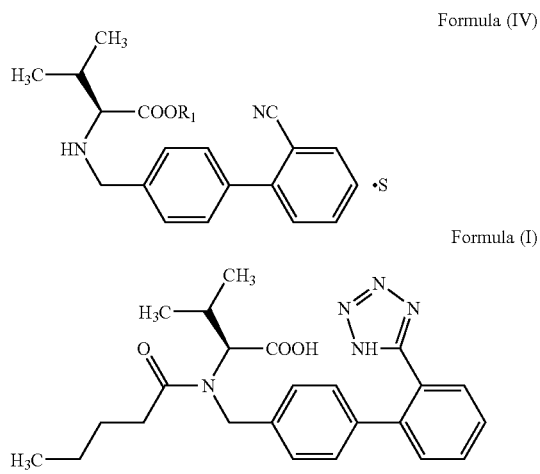

Formula (IV)

Formula (I)

wherein $R_1$ represents $C_1$-$C_4$ alkyl selected from methyl, ethyl, n-propyl, isopropyl, n-butyl, tert-butyl, 2-methylpropyl or benzyl and S represents organic acid selected from oxalic acid, acetic acid, formic acid, malic acid, maleic acid, malonic acid, succinic acid, fumaric acid, phthalic acid, terephthalic acid, citric acid, tartaric acid, methanesulfonic acid, ethanesulfonic acid, p-toluenesulfonic acid, trifluoroacetic acid, ascorbic acid and the like.

BACKGROUND OF INVENTION AND PRIOR ART

Valsartan belongs to group of angiotensin II antagonists which are useful in the treatment of hypertension, anxiety, glaucoma and cardiac attacks. Valsartan is an orally active specific angiotensin II antagonist acting on the AT1 receptor subtype. It is useful in regulating high blood pressure and cardiac insufficiency.

The process for preparing Valsartan is disclosed in U.S. Pat. No. 5,399,578 as shown by schematic diagram in Scheme-I:

Scheme-I:

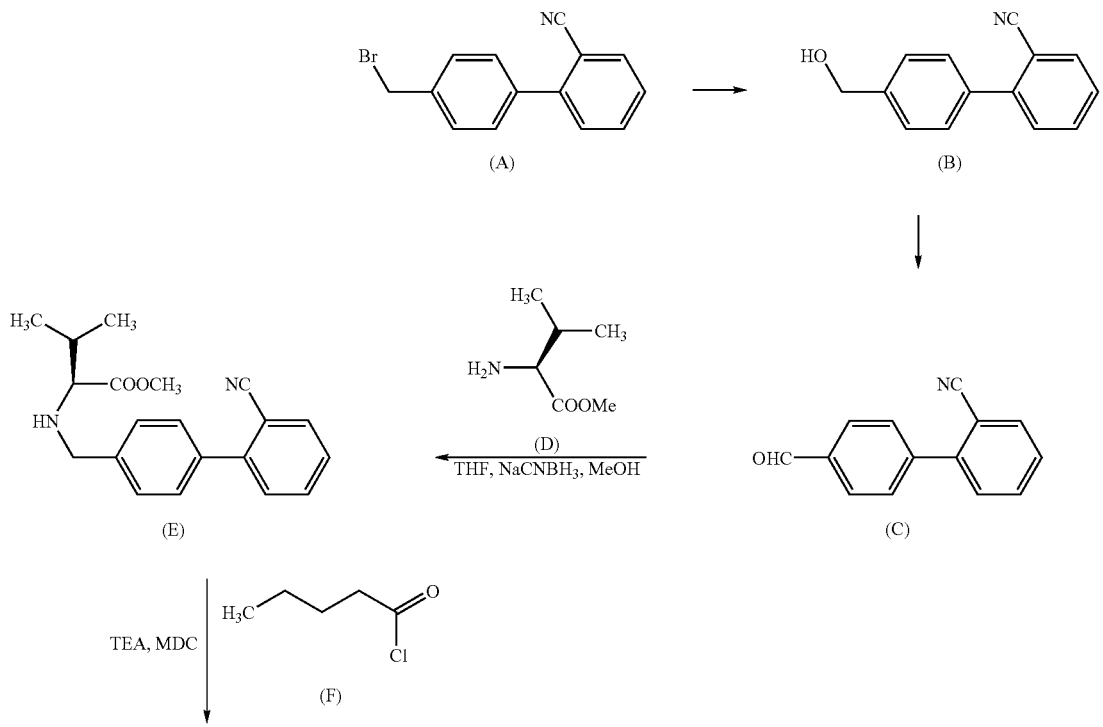

-continued

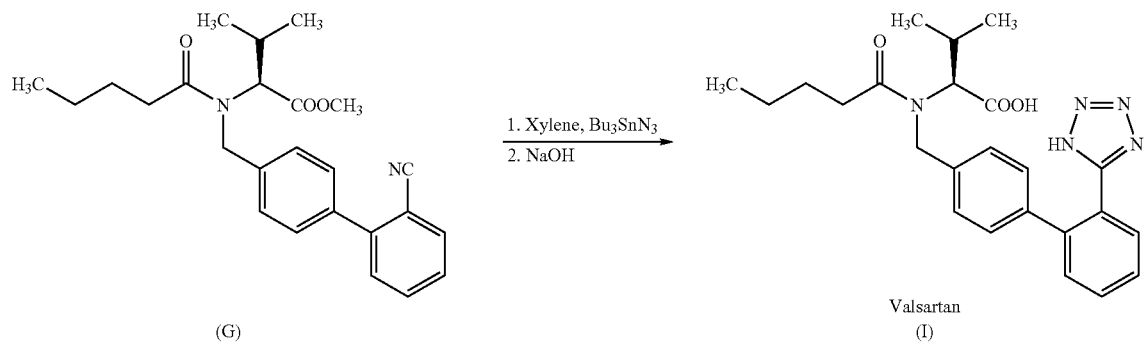

The synthesis involves the conversion of 4-bromomethyl-2'-cyanobiphenyl of formula (A) to carbaldehyde of formula (C). Further, it is condensed with methyl ester of L-valine of formula (D) under reducing condition to give N-[(2'-cyanobiphenyl-4-yl)methyl]-(L)-valine methyl ester of formula (E), which is purified by flash chromatography. Reaction of compound of formula (E) with n-Valeroyl chloride of formula (F) in presence of triethylamine gives N-valeryl-N-[(2'-cyanobiphenyl-4-yl)methyl]-(L)-valine methyl ester of formula (G). After purification by flash chromatography, compound of formula (G) is cyclized in presence of tributyltin azide in xylene and converted to Valsartan (I) in presence of sodium hydroxide.

The condensation of L-valine methyl ester and carbaldehyde requires reagent like sodium cyanoborohydride, which are costly. Also process involves purification of intermediates by flash chromatography, which is lengthy and cumbersome and difficult to adopt at commercial scale.

According to another embodiment given in U.S. Pat. No. 5,399,578 the carbaldehyde compound (C) is condensed with Tosylate salt of L-valine benzyl ester in presence of sodium cyanoborohydride to give benzyl ester analogue of compound of formula (E). This compound is purified by converting it into its hydrochloride salt and then breaking the hydrochloride salt with sodium bicarbonate. The purified compound is then reacted with n-Valeroyl chloride and cyclized with tributyltin azide in xylene. Further hydrogenation using Palladised carbon catalyst gives Valsartan (I).

The another approach for the synthesis of Valsartan is disclosed in general description of Bioorganic and Medicinal Chemistry Letters, Vol. 4 (1), 1994 as shown below in Scheme-II:

Scheme-II:
Synthesis of Aminoacid-derived Ang II antagonists

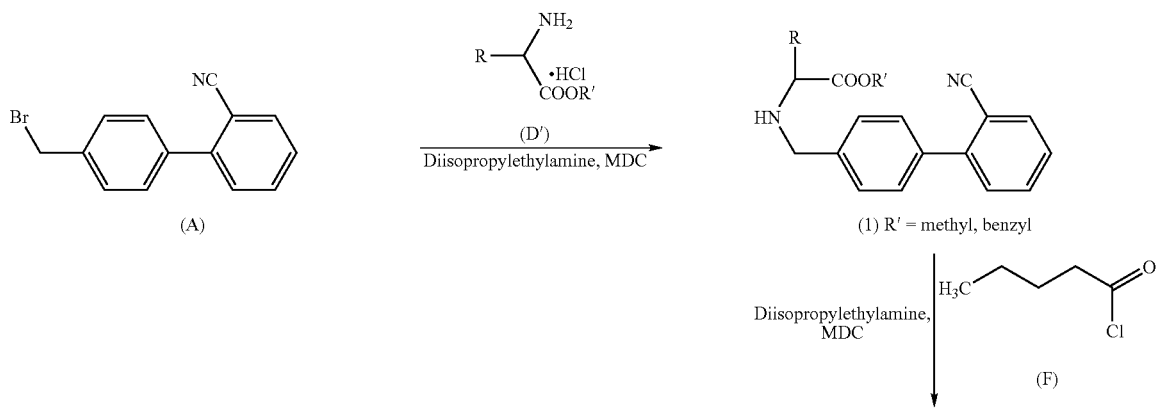

-continued

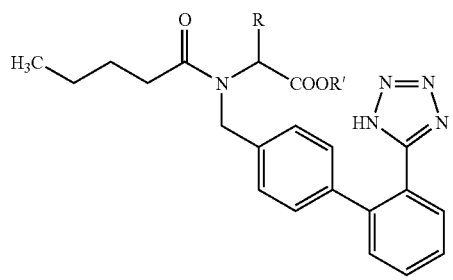

(3) R' = methyl, benzyl
(4) R' = H

1. Bu₃SnN₃, Xylene, reflux
2. Ester cleavage

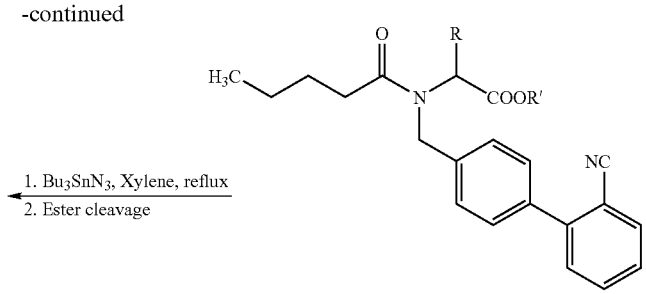

(2) R' = methyl, benzyl wherein R is —CH(CH₃)₂ in above scheme represents Valsartan(I).

So, the condensation of compound Halomethylbiphenyl derivative with L-valine ester is one of the important steps for the synthesis of Valsartan. It was observed by us that the condensation of compound of formula (II) with L-valine ester of formula (III) generates about 6-10% w/w unwanted dimeric impurity of formula (IVb) along with desired compound of formula (IVa) as shown in Scheme-III. This results in the poor yield and quality of the product and requires additional purification step.

column chromatography can be avoided. The compound of formula (IV) is stable and non-hygroscopic in nature. The use of compound (IV) in synthesis of Valsartan results in improved quality of product containing less percentage of impurities.

It was also surprisingly observed by us that condensation of compound of formula (IV) with n-valeroyl chloride of formula (F) takes place easily and rapidly in the presence of base and water, optionally in presence of organic solvent to give Scheme-III:

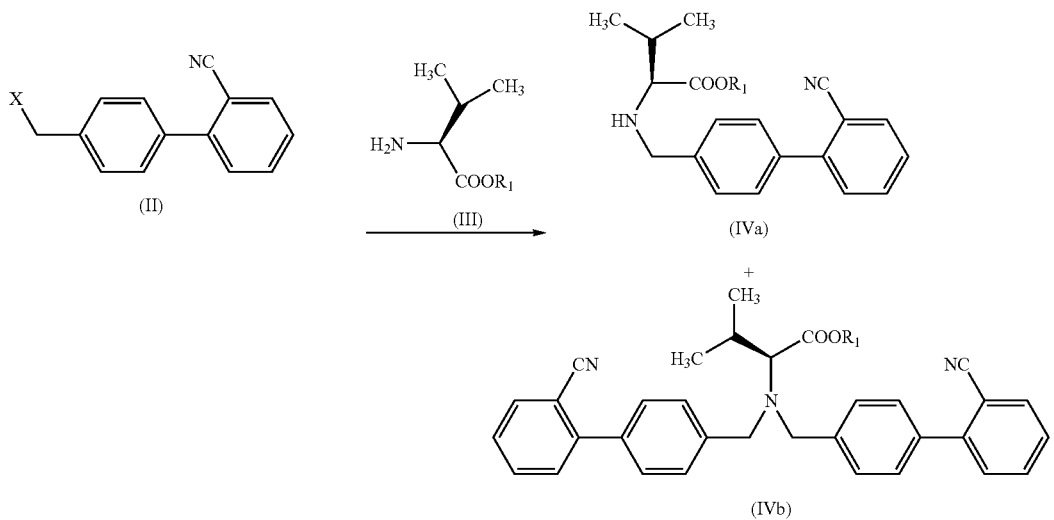

Therefore, there is a need to have simple, easy to handle and cost effective process for the preparation of Valsartan and its intermediates. Also, it is required to prepare its intermediate (IVa), substantially free from its dimeric impurity of formula (IVb).

The inventors of the present invention has surprisingly found that the dimeric impurity of formula (IVb) can be easily removed from desired compound of formula (IVa) by converting it into organic salt of formula (IV), which can be condensed directly with n-valeroyl chloride without further purification. Thus cumbersome technique of separation like compound of formula (VI). The crude compound of formula (VI) can be used further without purification to give Valsartan (I).

OBJECTS OF INVENTION

The object of the present invention is to provide an improved process for the preparation of Valsartan of formula (I).

Another object of the invention is to provide a novel compound of formula (IV) and its process for the preparation Yet another object of the present invention is to provide a process for preparing Valsartan by using novel intermediate, which is simple and easy to handle and cost effective.

SUMMARY OF INVENTION

Accordingly the principal aspect of the present invention relates to a novel compound of N-[(2'-cyanobiphenyl-4-yl)methyl]-(L)-valine ester organic acid salt of formula (IV)

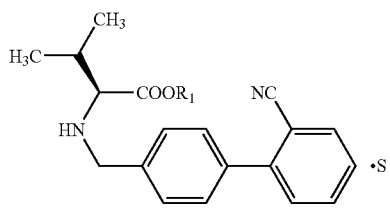

Formula (IV)

wherein $R_1$ represents $C_1$-$C_4$ alkyl selected from methyl, ethyl, n-propyl, isopropyl, n-butyl, tert-butyl, 2-methylpropyl or benzyl and S represents organic acid selected from oxalic acid, acetic acid, formic acid, malic acid, maleic acid, malonic acid, succinic acid, fumaric acid, phthalic acid, terephthalic acid, citric acid, tartaric acid, methanesulfonic acid, ethanesulfonic acid, p-toluenesulfonic acid, trifluoroacetic acid, ascorbic acid and the like.

According to another aspect of the invention, there is provided a process for preparing organic acid salt of N-[(2'-cyanobiphenyl-4-yl)methyl]-(L)-valine ester of formula (IV) comprising:

(a) reacting 4-halomethyl-2'-cyanobiphenyl of formula (II)

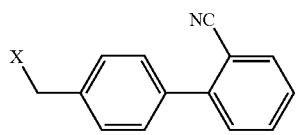

Formula (II)

wherein X represents halogen selected from Cl or Br, with L-Valine ester derivative of formula (III)

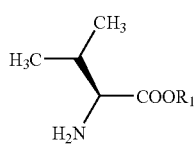

Formula (III)

wherein $R_1$ represents $C_1$-$C_4$ alkyl selected from methyl, ethyl, n-propyl, isopropyl, n-butyl, tert-butyl, 2-methylpropyl or benzyl; in presence of base and solvent, optionally in presence of catalyst; to form N-[(2'-cyanobiphenyl-4-yl)methyl]-(L)valine ester derivative of formula (IVa).

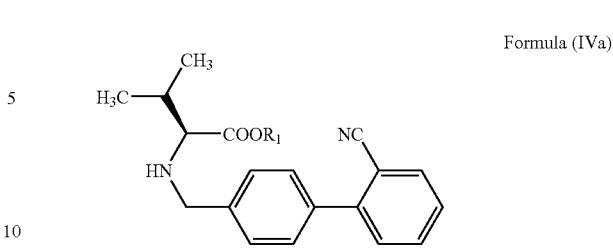

Formula (IVa)

wherein $R_1$ represents $C_1$-$C_4$ alkyl selected from methyl, ethyl, n-propyl, isopropyl, n-butyl, tert-butyl, 2-methylpropyl or benzyl.

(b) treating N-[(2'-cyanobiphenyl-4-yl)methyl]-(L)-valine ester derivative of formula (IVa) with organic acid to obtain compound of formula (IV).

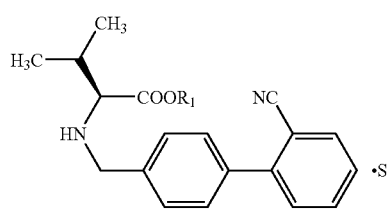

Formula (IV)

wherein $R_1$ represents $C_1$-$C_4$ alkyl selected from methyl, ethyl, n-propyl, isopropyl, n-butyl, tert-butyl, 2-methylpropyl or benzyl; S represents organic acid selected from oxalic acid, acetic acid, formic acid, malic acid, maleic acid, malonic acid, succinic acid, fumaric acid, phthalic acid, terephthalic acid, citric acid, tartaric acid, methanesulfonic acid, ethanesulfonic acid, p-toluenesulfonic acid, trifluoroacetic acid, ascorbic acid and the like.

According to a further aspect of the invention there is provided a process for the preparation of Valsartan (I) comprising:

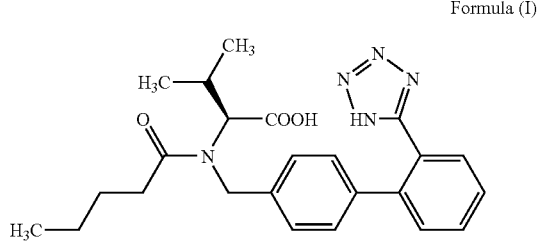

Formula (I)

(a) reacting 4-halomethyl-2'-cyanobiphenyl of formula (II)

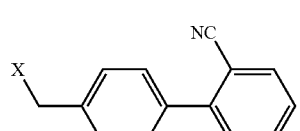

Formula (II)

wherein X represents halogen selected from Cl or Br, with L-valine ester derivative of formula (III)

Formula (III)

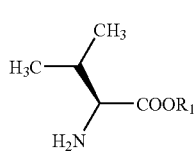

wherein $R_1$ represents $C_1$-$C_4$ alkyl selected from methyl, ethyl, n-propyl, isopropyl, n-butyl, tert-butyl, 2-methylpropyl or benzyl; in presence of base and solvent, optionally in presence of catalyst; to form N-[(2'-cyanobiphenyl-4-yl)methyl]-(L)-valine ester derivative of formula (IVa)

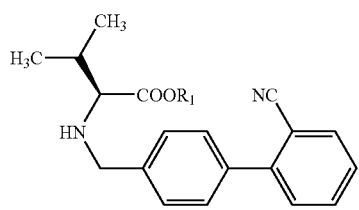

Formula (IVa)

wherein $R_1$ represents $C_1$-$C_4$ alkyl selected from methyl, ethyl, n-propyl, isopropyl, n-butyl, tert-butyl, 2-methylpropyl or benzyl;

(b) treating N-[(2'-cyanobiphenyl-4-yl)methyl]-(L)-valine ester derivative of formula (IVa) with organic acid to obtain compound of formula (IV).

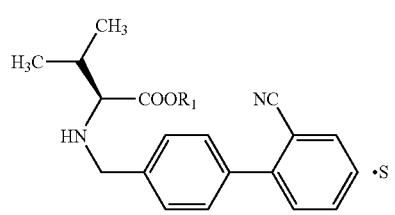

Formula (IV)

wherein $R_1$ represents $C_1$-$C_4$ alkyl selected from methyl, ethyl, n-propyl, isopropyl, n-butyl, tert butyl, 2-methylpropyl or benzyl; S represents organic acid selected from oxalic acid, acetic acid, formic acid, malic acid, maleic acid, malonic acid, succinic acid, fumaric acid, phthalic acid, terephthalic acid, citric acid, tartaric acid, methanesulfonic acid, ethanesulfonic acid, p-toluenesulfonic acid, trifluoroacetic acid, ascorbic acid and the like (c) acylating the compound of formula (IV) with Valeroyl halide of formula (V)

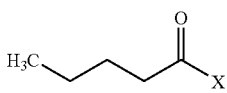

Formula (V)

wherein X is halogen selected from Cl or Br; in the presence of base and water, optionally in organic solvent; to obtain compound of formula (VI)

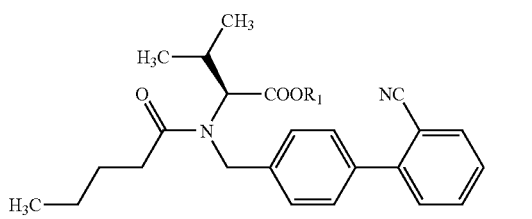

Formula (VI)

wherein $R_1$ represents $C_1$-$C_4$ alkyl selected from methyl, ethyl, n-propyl, isopropyl, n-butyl, tert-butyl, 2-methylpropyl or benzyl (d) Converting the compound of formula (VI) to obtain compound formula (I) by the method such as here in described or by the conventional method.

According to yet another aspect, there is provided a method of preparing compound of formula (IV) which is substantially free from dimeric impurity of formula (IVb).

According to yet further aspect of the invention there is provided a novel compound of formula (IV) which is organic acid salt of N-[(2'-cyanobiphenyl-4-yl)methyl]-(L)-valine ester.

DETAILED DESCRIPTION OF INVENTION

N-[(2'-cyanobiphenyl-4-yl)methyl]-(L)-valine ester of formula (IVa) is an useful intermediate for the synthesis of Valsartan (I). It can be prepared by reaction of 4-halomethyl-2'-cyanobiphenyl of formula (II) with L-valine ester derivative of formula (III). It is observed that this reaction gives compound of formula (IVa) containing about 6-10% by weight of unwanted dimeric impurity of formula (IVb). This impurity is difficult to remove by conventional methods of purification such as crystallization and column chromatography. Moreover, this results in the poor yield and quality of Valsartan and requires additional purification.

The inventors of the present invention found the novel compound of formula (IV), which is an organic acid salt of N-[(2'-cyanobiphenyl-4-yl)methyl]-(L)-valine ester, which does not yields the dimeric impurity and does not require additional purification. The novel compound of formula (IV) is substantially free form the dimeric impurity of formula (IVb).

The reaction of 4-halomethyl-2'-cyanobiphenyl of formula (II) with L-valine ester derivative of formula (III) is carried out in presence of base in solvent. The base can be selected from the group comprising of organic base, inorganic base or mixtures thereof, more preferably sodium hydroxide, potassium hydroxide, calcium hydroxide, magnesium hydroxide, sodium bicarbonate, potassium bicarbonate, sodium carbonate, potassium carbonate, cesium carbonate, sodium methoxide, potassium methoxide, sodium ethoxide, potassium ethoxide, potassium tert-butoxide, ammonia, triethyl amine, pyridine and the like and most preferably sodium carbonate and potassium carbonate. Solvent can be selected form dimethylformamide, dimethylsulfoxide, acetonitrile, xylene or toluene, halogenated hydrocarbon such as methylenedichloride, ethylenedichloride or chloroform, alcohol such as methanol, ethanol, n-propanol, isopropanol, n-butanol, isobutanol, tert-butanol, n-Amyl alcohol, isoamyl alcohol or tert-amyl alcohol or mixtures thereof.

The reaction is carried out optionally in presence of catalyst selected from alkaline earth metal halide like sodium iodide or potassium iodide. It acts as a promoter or an activator for condensation of halogen compound of formula (II) with L-valine ester derivative of formula (III).

The reaction is carried out at temperature ranging from about 0° C. to about boiling temperature of the solvent, more preferably at about 30° C. to about 50° C. The reaction time varies from about 1 hour to about 10 hours, more preferably from about 2 hours to about 5 hours.

After the completion of reaction, it is converted to organic acid salt of formula (IV) by treating it with organic acid optionally in presence of solvent.

The organic acid can be selected from group comprising of oxalic acid, acetic acid, formic acid, malic acid, maleic acid, malonic acid, succinic acid, fumaric acid, phthalic acid, terephthalic acid, citric acid, tartaric acid, methanesulfonic acid, ethanesulfonic acid, p-toluenesulfonic acid, trifluoroacetic acid, ascorbic acid and the like. Solvent can be selected from water, methanol, ethanol, propanol, isopropanol, tert-butanol, toluene, n-hexane, o-xylene, n-heptane, methylenedichloride, ethylenedichloride, acetonitrile, dimethylformamide, dimethylsulfoxide or mixture thereof, more preferably water, o-xylene or mixtures thereof. The conversion takes place in about 5 hours, more preferably in about 1 hour. The organic acid salt of formula (IV) is then isolated and dried by conventional methods.

In one of the preferred embodiments 4-bromomethyl-2'-cyanobiphenyl, L-valine methyl ester, potassium carbonate and potassium iodide are taken in acetonitrile. The reaction mixture was stirred at about 40-45° C. for about 3 to 4 hours and the solvent was removed under vacuum. Water and xylene was added to reaction mass and the organic layer was separated. A solution of oxalic acid was added to the organic layer and stirred for about an hour at ambient temperature to give N-[(2'-cyanobiphenyl-4-yl)methyl]-(L)-valine methyl ester oxalate salt.

The condensation step of compound of formula (IV) with valeroyl halide of formula (V), wherein X is halogen selected from Cl or Br, is carried out in presence of base and water, optionally in organic solvent, to give compound of formula (VI).

Base can be selected from sodium hydroxide, potassium hydroxide, calcium hydroxide, magnesium hydroxide, sodium bicarbonate, potassium bicarbonate, sodium carbonate, potassium carbonate, cesium carbonate, sodium methoxide, potassium methoxide, sodium ethoxide, potassium ethoxide, potassium tert-butoxide, ammonia, triethyl amine, pyridine and the like, more preferably sodium carbonate or potassium carbonate. Solvent can be selected from group comprising of methylene dichloride, chloroform, ethylene dichloride, xylene, toluene, dimethylformamide, dimethylacetamide, dimethylsulfoxide, more preferably xylene.

The reaction is carried out in temperature ranging form about 0° C. to the boiling point of the solvent, more preferably from about 0° C. to about 45° C. and most preferably at about 0° C. to about 5° C. The reaction takes place in about 1 hour to about 10 hours, more preferably about 2 hours to about 3 hours.

After completion of the reaction, the compound of formula (VI) is isolated by regular work-up procedures and can be used in the next step of cyclization without further purification. Alternatively after the reaction is over, the reaction mixture is washed with aqueous basic solution to bring pH to neutral and the organic layer is separated. The organic layer can be used directly for the next step of cyclization without isolating compound of formula (IV).

Conversion of compound of formula (IV) to Valsartan of formula (I) can be carried out by conventional methods reported in prior art like use of tributyltin azide, tributyltin chloride and sodium azide, etc. in presence of solvent and subsequent de-protection. De-protection can be carried out in presence of base and solvent or by catalytic hydrogenation depending on the nature of L-valine ester derivative (III)

According to one of the preferred embodiments, N-[(2'-cyanobiphenyl-4-yl)methyl]-(L)-valine methyl ester oxalate salt was taken in xylene followed by addition of aqueous potassium carbonate solution and valeroyl chloride at about 0-5° C. After completion of the reaction, the organic layer was washed with basic solution of sodium bicarbonate and separated. Tributyltin chloride and sodium azide was added to the organic layer and refluxed for about 20-25 hours. Further 10% sodium hydroxide solution was added to it and stirred for about 20-25 hours at ambient temperature to facilitate deprotection of methyl group. After regular work-up procedures, Valsartan was obtained.

Valsartan can be purified by conventional methods. Alternatively it is possible to purify Valsartan by base-acid treatment. The crude Valsartan is dissolved in solvent preferably dichloromethane and solution of aqueous base preferably sodium bicarbonate is added to it till neutral pH. Further the layers are separated to remove impurities and the aqueous layer is charcoalized and filtered. Then organic solvent preferably dichloromethane is added to it and the pH is adjusted to about 3-4 using acetic acid. The organic layer is separated and concentrated to obtain residue. Cyclohexane is added to this residue to form slurry which is stirred at ambient temperature for about an hour followed by filtration to obtain pure Valsartan.

Following examples illustrate the process of invention. However, these do not limit the scope of present invention.

EXAMPLE 1

Preparation of N-[(2'-cyanobiphenyl-4-yl)methyl]-(L)-valine methyl ester oxalate salt 100 g 4-Bromomethyl-2'-cyanobiphenyl is added to 500 ml acetonitrile followed by 69 g of anhydrous potassium carbonate, 12 g potassium iodide and 65 g L-Valine methyl ester. The reaction mixture is stirred at 40-45° C. for 3-4 hours. After completion of the reaction, the reaction mixture is filtered and acetonitrile is removed under vacuum at 45-50° C. 300 ml of water and 300 ml of o-xylene are added to the residue and the layers are separated. Solution of 50 g oxalic acid in 500 ml water is added to the organic layer and stirred for about an hour and filtered. The solid is washed and then dried under vacuum at 50-55° C. (yield: 130-135 g).

EXAMPLE 2

Preparation of Valsartan 100 g oxalate salt obtained in Example 1 and 119 g. of Potassium carbonate are added to 400 ml o-xylene and 400 ml water and cooled to 0-5° C. 44.5 g valeroyl chloride is added to the reaction mixture over a period of 1 to 1.5 hours and stirred for about 1.5 to 2 hours at 0-5° C. After completion of the reaction, the layers are separated and the organic layer is washed with 400 ml 5% sodium bicarbonate solution. 160 g tributyltin chloride and 59 g sodium azide are added to organic layer and heated to reflux for about 20-25 hours. The reaction mixture is cooled to ambient temperature and a 1000 ml of 10% sodium hydroxide solution is added to the reaction mixture and stirred at ambient temperature of 20-25 hours. After the completion of the reaction, layers are separated and 1000 ml dichloromethane is added to the aqueous layer, 200 ml of acetic acid is added to it till pH 3-4 is obtained and stirred for about 30 minutes. The layers are separated and the organic layer is washed with brine solution.

1000 ml 5% sodium bicarbonate solution is added to the organic layer and stirred for 10-12 hours at room temperature. Layers are separated and 1000 ml dichloromethane is added to aqueous layer. 100 ml acetic acid is added to it till pH 3 to 4 and layers are separated. The organic layer is washed with water and distilled out under vacuum at 40-45° C. 200 ml cyclohexane is added to the residue and stripped out. Finally 700 ml cyclohexane is added to the residue to form slurry which is stirred for about half an hour and filtered. The crude Valsartan is dried under vacuum at 40-45° C. (yield: 40-45 g).

The invention claimed is:

1. An organic acid salt of N-[(2'-cyanophenyl-4-yl)methyl]-(L)-valine ester of formula (IV)

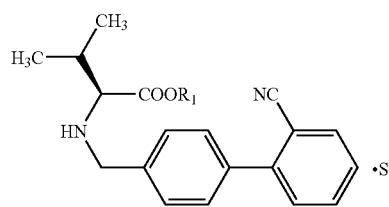

Formula (IV)

wherein $R_1$ represents $C_1$—$C_4$ alkyl selected from the group consisting of methyl, ethyl, n-propyl, isopropyl, n-butyl, tert-butyl, and 2-methylpropyl, or benzyl, and S represents organic acid selected from the group consisting of oxalic acid, acetic acid, formic acid, malic acid, maleic acid, malonic acid, succinic acid, fumaric acid, phthalic acid, terephthalic acid, citric acid, tartaric acid, methanesulfonic acid, ethanesulfonic acid, p-toluenesulfonic acid, trifluoroacetic acid, and ascorbic acid.

2. The organic salt of N-[(2'-cyanophenyl-1-4-yl)methyl]-(L)-valine ester of formula (IV) according to claim 1, wherein $R_1$ represents methyl or ethyl or benzyl, and S represents oxalic acid.

3. An organic acid salt of N-[(2'-cyanophenyl-4-yl)methyl]-(L)-valine ester of formula (IV), which is substantially free from dimeric impurity of formula (IVb)

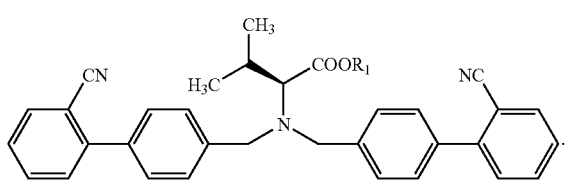

(IVb)

4. Use of an organic acid salt of N-[(2'-cyanophenyl-4-yl)methyl]-(L)-valine ester of formula(IV)

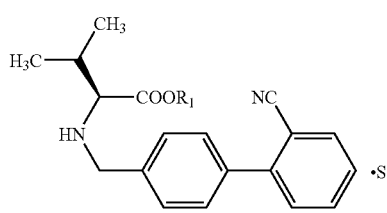

Formula (IV)

wherein $R_1$ represents $C_1$—$C_4$ alkyl selected from the group consisting of methyl, ethyl, n-propyl, isopropyl, n-butyl, tert-butyl, and 2-methylpropyl, or benzyl, and S represents organic acid selected from the group consisting of oxalic acid, acetic acid, formic acid, malic acid, maleic acid, malonic acid, succinic acid, fumaric acid, phthalic acid, terephthalic acid, citric acid, tartaric acid, methanesulfonic acid, ethanesulfonic acid, p-toluenesulfonic acid, trifluoroacetic acid, and ascorbic acid in synthesis of Valsartan (I).

* * * * *